United States Patent [19]

Taff et al.

[11] 4,447,225
[45] May 8, 1984

[54] MULTIDOSE JET INJECTOR

[76] Inventors: Barry E. Taff, 8665 Pickford St., Los Angeles, Calif. 90035; Kenneth P. Stoller, 341 S. Bentley Ave., Los Angeles, Calif. 90049

[21] Appl. No.: 360,333

[22] Filed: Mar. 22, 1982

[51] Int. Cl.³ .............................................. A61M 5/00
[52] U.S. Cl. ...................................................... 604/71
[58] Field of Search ........................ 604/71, 68, 48, 19

[56] References Cited

U.S. PATENT DOCUMENTS

| | | | |
|---|---|---|---|
| 3,138,157 | 6/1964 | Ziherl et al. | 604/71 |
| 3,202,151 | 8/1965 | Kath | 604/71 |
| 3,330,276 | 7/1967 | Gordon | 604/71 |
| 3,805,783 | 4/1974 | Ismach | 604/71 |
| 4,059,107 | 11/1977 | Iriguchi et al. | 604/71 |

Primary Examiner—John D. Yasko
Attorney, Agent, or Firm—Philip D. Junkins

[57] ABSTRACT

A multidose jet injector having a main cylindrical body assembly with a jet discharge orifice in its closed forward end and which encloses an internal injector piston element. The piston element can be cocked against heavy spring pressure and, in its cocked position, defines a medicament delivery chamber between the closed end of the main body assembly and the head of the piston. A reciprocative piston puller element is located within the main body assembly, rearward of the piston element, and is connected to a medicament pump cylinder which is enclosed within an elongated rearward tubular portion of the piston element. The puller element is used to pull the piston element to its cocked position and thereafter to reciprocate the medicament pump cylinder to first aspirate a controlled volume of medicament liquid from its supply vial to a medicament transfer chamber (formed within the rearward section of the tubular portion of the piston element) and then pump such medicament via a cannula passageway through the pump body and injector piston to the medicament delivery chamber. The main cylindrical body assembly includes a medicament apportionment mechanism which simultaneously adjusts the respective volumes of the medicament delivery chamber and medicament transfer chamber to allow for changes in desired medicament dosage quantities. Upon release of the injector piston from its cocked position, spring pressure imparts fast and powerful movement to such piston and medicament is ejected from the delivery chamber through the discharge orifice of the injector.

14 Claims, 8 Drawing Figures

MULTIDOSE JET INJECTOR

BACKGROUND OF THE INVENTION

1. Field of the Invention:

The present invention relates to an improved hand-held, multidose jet injection apparatus which is particularly suited as a hypodermic jet injector for the injection of medical liquids through the outer skin surface of either humans or animals under sufficiently high pressure to force the liquids to a predetermined depth within the tissues beneath the skin surface. Thus, the apparatus is suitable for the needleless delivery of both subcutaneous and intra-muscular injections.

2. Description of the Prior Art:

Over the past thirty-five years there have been proposed a multitude of hypodermic jet injector devices for the injection of set amounts of medical liquids such a vaccines, medicaments, anesthetics, and the like, without the use of needles. Conventional jet injection devices have a medicament chamber for holding an injectable liquid, a piston for pressurizing the injectable liquid and a nozzle hole or orifice for ejecting the injectable liquid. Such devices have advantages over the classic syringe devices comprised of a syringe cylinder, piston and hypodermic needle in that a needleless jet injection can be effected within a much shorter time and there is no requirement of a newly sterilized needle for every injection.

Only a few of the proposed hypodermic jet injector device designs have been incorporated in commercially available needleless injection apparatus. A needleless injector for diabetics to use for the self-administration of insulin has been marketed by the Derata Corporation under the trademark "Medi-Jector." This hand-held jet injection device is principally designed to deliver subcutaneous insulin injections to a single patient. The device is adjustable as to the volume of medicament delivered and receives the medicament from a vial supported by, and projecting from, the injection delivery end of the device. The power source for ejecting the medicament comprises a number of internal springs which when released (after being compressed) drive a piston which forces the medicament under high pressure through the nozzle at the injection delivery end of the device.

Another hand-held jet injection device for diabetics has been marketed by Mizzy, Inc. under the trademark "SyriJet." A multidose insulin cartridge is side-loaded into the device. Driving power for the medicament is derived from self-contained springs.

There remains a tremendous need for small, portable, hand-held and hand-operated jet injectors which are capable of administering both subcutaneous and intra-muscular multidose injections of a wide variety of medicaments, vaccines, anesthetics and other medical liquids and which can be manipulated under sterile transfer conditions to receive, mix and administer two or more medical liquids as a mixed dose without the entrapment of air.

SUMMARY OF THE INVENTION

The prior art jet injection devices are generally limited to low volume needleless injections in the order of one-tenth to one-half cubic centimeters of medicament. Such low volume injections limit the suitability of these devices to subcutaneous administration of medical liquids. A most serious problem, with the presently available devices, is that of air entrapment within the instrument together with the liquid to be injected. Such entrapped air reduces the efficiency of the injection procedure because the air acts as a pressure cushion to reduce the required initial high peak pressure and to thus reduce the velocity of the skin-penetrating stream of injected liquid. If there is more than a mere nominal amount of air present with the liquid in the injection device, the cushioning effect may cause it to fail to operate. Further, the presence of more than nominal quantities of air in the liquid chamber prior to the injection procedure may lead to uncertainty as to the real volume of the dose of the liquid.

Air entrapment presents an even greater problem when it is desired to manipulate an injection device (either of classic needle-syringe type or jet injection type) so as to combine two or more medical liquids to form a mixed dose. Further, when air becomes mixed with the injection liquid in its pre-injection chamber a certain portion of the air will be injected together with the liquid into the skin of the patient and thus causes undesired discomfort and distress to the patient, and may cause an embolism.

It is an object of the present invention to provide an improved hand-held, multidose jet injector apparatus which is readily adjustable as to the volume of the dose of medical liquid received by the apparatus from a medical liquid vial and within which medical liquid is transferred to an ejection chamber and is ejected therefrom without the entrapment of air.

Another object of the present invention is to provide an improved hand-held jet injector apparatus which is capable of receiving, mixing and administering two or more medical liquids as a mixed dose without the entrapment of air.

A further object of the invention is to provide an improved hand-held jet injector apparatus which is powered by self-contained spring means capable of needleless delivery of both subcutaneous and intra-muscular injections.

A still further object of the invention is to provide an improved multidose jet injector apparatus which is essentially self-cleaning and which provides a minimum of internal surface area to be contacted by the medical liquid so that it is possible to change the liquid to be injected by the apparatus merely by changing the medical liquid supply vial and purging the remnants of prior liquid by operating the apparatus with the new liquid.

It is a still further object of the present invention to provide an improved hand-held jet injector apparatus which is capable of receiving sequentially equal or unequal volumes of two or more medical liquids from their respective vials and of mixing such liquids and administering the same by needleless injection as a mixed dose, without the entrapment of air.

In accordance with the invention, in addition to the above objects, the apparatus of the present invention provides various important advantages, including simplicity of construction and ease of operation and cleaning.

Further objects and advantages of the invention will be apparent from the following specification and accompanying drawings.

In carrying out the present invention in one preferred form thereof, there is provided an improved multidose hypodermic jet injector apparatus having a main cylindrical body assembly with a jet discharge orifice in the closed forward end thereof. The main body assembly encloses a shiftable internal injector piston element which can be cocked against heavy spring pressure and which, in its cocked position, defines a variable volume medicament delivery chamber between the closed forward end of the main body assembly and the head portion of such piston element. A reciprocative piston puller element is located within the main body assembly of the jet injector apparatus rearward of the piston element and is connected to a medicament pump cylinder which is enclosed within an elongated rearward tubular portion of the piston element. The puller element is used to pull the piston element to its cocked position and thereafter to reciprocate the medicament pump cylinder to first aspirate a controlled volume of medicament liquid from its supply vial to a variable volume medicament transfer chamber (formed within the rearward section of the elongated tubular portion of the piston element) and then pump such volume of medicament from the transfer chamber via a cannula passageway through the pump body and the injector piston body to the medicament delivery chamber.

The main cylindrical body assembly is surrounded by a cylindrical medicament apportionment mechanism including a rotatable regulating cylinder which, through its rotation, simultaneously positions piston stops and pump stops whereby the respective volumes of the medicament delivery chamber and medicament transfer chamber are adjusted for changes in desired medicament dosage quantities. After transfer of the medicament from the rearward transfer chamber to the forward delivery chamber and placement of the jet injector apparatus, including the jet discharge orifice, in appropriate injection position with respect to the injection site of a patient, the injector piston element is released from its cocked position and the heavy spring pressure imparts a fast and powerful movement force to the injector piston element in a direction to reduce the volume of the delivery chamber to cause ejection of the medicament from the delivery chamber through the discharge orifice with sufficient force to penetrate the skin of the patent and into underlying tissue and muscle areas at the injection site. Through sequential adjustment of the rotatable regulating cylinder and cocking of the piston injector element, with appropriate manipulation of the medicament pump, two or more different medical liquids may be sequentially introduced into the transfer chamber and transferred to the delivery chamber of the injector appraratus for mixing and subsequent ejection through the discharge orifice, without the entrapment of air.

DESCRIPTION OF THE PREFERRED EMBODIMENT

Figure 1:
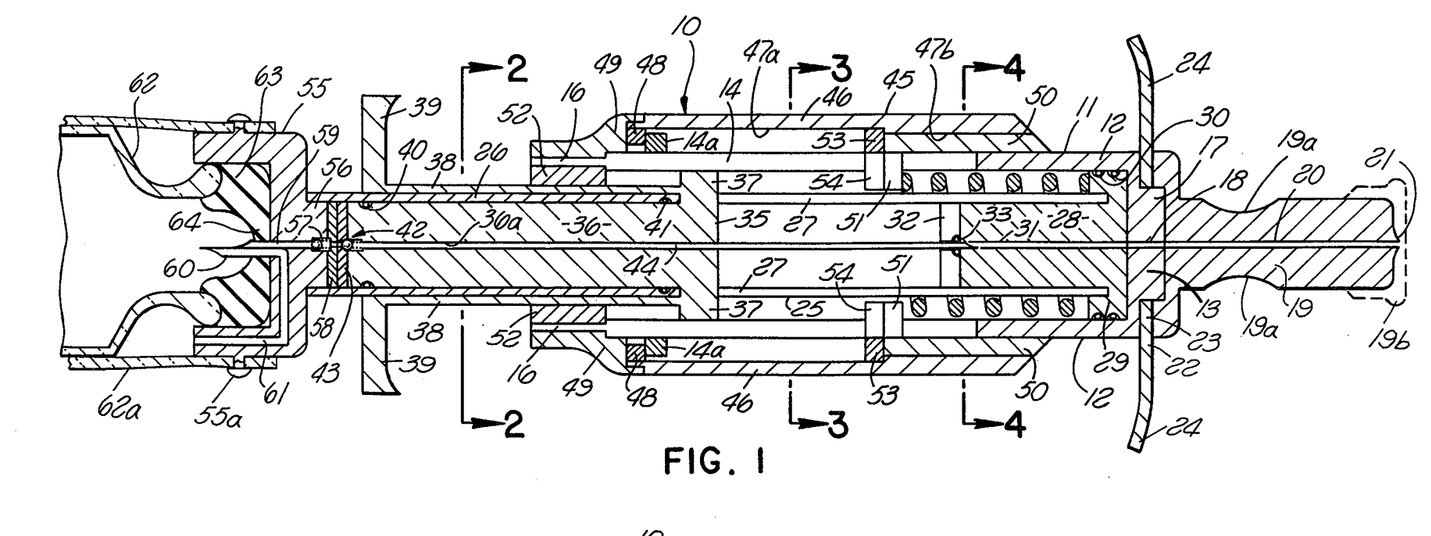
FIG. 1 is a side cross-sectional view of a jet injector apparatus constructed in accordance with the present invention and in which the injector piston element is in its forward uncocked position and the medicament pump is in its rearward position whereby the rearward medicament transfer and forward medicament delivery chambers of the apparatus have zero volume and the apparatus is free of medicament liquid.
Figure 3:
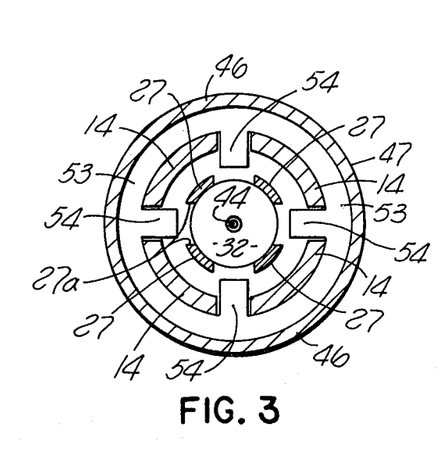
FIG. 3 is another sectional view of the injector apparatus of FIG. 1 taken on line 3—3 of FIG. 1.
Figure 4:
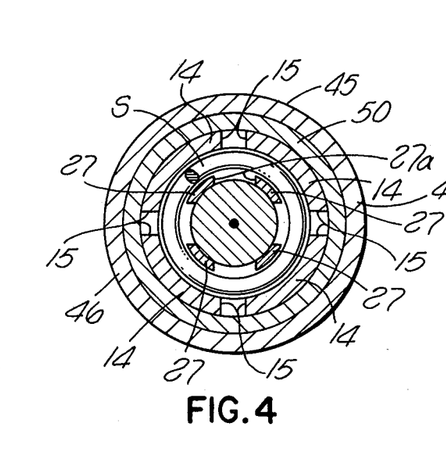
FIG. 4 is a further sectional view of the injector apparatus of FIG. 1 taken on line 4—4 of FIG. 1.

FIG. 1 illustrates the improved multidose jet injector apparatus of this invention in a cross-sectional view. The injector apparatus 10 has the general appearance of an elongated device which includes a main body assembly 11 comprised principally of tubular member 12 having a closed end wall 13 at its forward end and arcuate leg portions 14 extending rearwardly, such leg portions defining slots 15 therebetween and including arcuate leg extension portions 16 of reduced thickness. The configurations and structural relationships of arcuate leg portions 14 and slots 15 are shown in FIGS. 3 and 4. The closed end wall 13 of tubular member 12 includes a projecting portion 17 with a relatively small, centrally-positioned passageway or orifice 18 leading therethrough. The projecting portion 17 of end wall 13 provides mounting support for injector nose piece 19 which includes orifice 20 which mates with orifice 18 and terminates in a tip portion 21 of the nose piece. A hilt element 22, comprised of hilt ring 23 and a pair of hilt grip members 24, is mounted on the projecting portion 17 of end wall 13 between such wall and the nose piece 19. The nose piece 19 may be interchangeable with other nose pieces to provide a series of orifice diameters and/or a variety of nose piece lengths, diameters and angular configurations. As shown, the nose piece 19 is provided with finger notches 19a and the orifice 20 and tip portion 21 thereof may be protected, when the injector is not in use, by a cap or closure member 19b shown in dotted line configuration.

Located within the tubular member 12 of the main body assembly 11 is an internal piston assembly 25 comprised of tubular member 26 with arcuate piston leg portions 27 extending forwardly, such leg portions defining slots 27a therebetween. A piston head member 28 is mounted within the leg portions 27 at their forward end and includes piston head portion 29 of diameter greater than the tubular member 26 and of matching diameter to the inner wall surface of tubular member 12. The head portion 29 of the piston element 25 is in reciprocable engagement with the inner wall of member 12 and is provided with one or more seal rings 30 to prevent the leakage of liquid between member 12 and the piston head portion 29. A centrally-positioned passageway or orifice 31 extends throughout the length of piston head member 28 and is in alignment with orifice 18 in end wall 13. A seal plate 32 is affixed to the rearward end of piston member 28. This plate includes centrally-positioned orifice 32a, which is in alignment with orifice 31 of member 28, and maintains an O ring seal 33 in position at the rearward end of orifice 31.

Mounted within the rearward portion of tubular member 26, and reciprocative with respect thereto, is a piston puller device 35. This device is comprised of: a medicament pump cylinder 36 slidably positioned within member 26; piston puller projections 37 which extend radially from pump cylinder 36 (at its forward end through the slots 27a) and abut in sliding contact with the inner wall of arcuate legs 14 of tubular member 12; and a pair of piston puller arms 38 which extend rearwardly from two of the projections 37 (outside of tubular member 26) and terminate (in the proximity of the rearward end of pump cylinder 36 but outside of member 12) as a pair of puller finger grips 39. The pump cylinder 36 is provided at its rearward end with an O ring seal 40 interfacing with the inner wall of tubular member 26 and such member is provided at its forward end (before its extension as legs portions 27) with an O ring seal 41 interfacing with the outer surface of pump cylinder 36.

The medicament pump cylinder 36 contains a centrally-positioned passageway or orifice 36a which extends throughout the length of the pump cylinder and is in alignment with orifice 31 in piston head member 28. At its rearward end, orifice 36a leads into a one-way ball valve 42 of well-known ball and spring design. The ball and spring of valve 42 are maintained in seated position at the rearward end of pump cylinder 36 by valve cover plate 43 which is affixed to the end of cylinder 36 and has a centrally-positioned opening in allignment with orifice 36a and the intervening ball of valve 42. The ball of valve 42 seats into the opening in plate 43 and the ball is maintained in closed position by its associated spring whereby liquid may pass forwardly into and through orifice 36a, but is precluded from rearward flow through the valve. Located within orifice 36a of the pump is cannula 44 which: extends from the rearward end of the pump cylinder to the forward end thereof; projects across space A (formed within the leg portions 27 of tubular member 26 and defined at its rearward end by puller device 35 and at its forward end by plate 32 of piston member 28); and terminates at its sharpened, piercing end within orifice 31 of piston member 28 after passing through O ring seal 33 at the rearward end of orifice 31. Through the cannula 44 passageway, communication for liquid flow is effected from the ball valve 42, at the rearward end of pump cylinder 36, to the tip portion 21 of the nose piece 19 of the jet injector 10.

Surrounding, and interconnected with, main body assembly 11 of the jet injector 10 is a medicament apportionment mechanism 45 comprised principally of: a rotatable medicament quantity regulating cylinder 46 (having internal threaded wall portions 47a and 47b); a locking ring 48 (threaded to wall portion 48a of cylinder 46); an end bearing member 49 (threaded to reduced leg portions 16 of tubular member 12); and an indicia cylinder 50 (threaded to wall portion 47b of cylinder 46 and positioned between such cylinder and tubular member 12) for slideable indicia movement along such member toward and from the forward end of jet injector 10. The indicia cylinder 50 is provided with spring-positioning pawls 51 which project in radial inwardly fashion within slots 15 of tubular member 12. At the rearward end of the medicament apportionment mechanism 45 there is provided a split closure ring 52 which, at its outer periphery, is threaded to the inner surface of the extension portions 16 of arcuate legs 14 of tubular member 12. The closure ring 52 acts as a stop for the piston puller device 35 in that, when such device is in its most rearward position, projections 37 of the device are stopped from further rearward movements by the forward face of such ring (See FIG. 5).

Figure 1A:
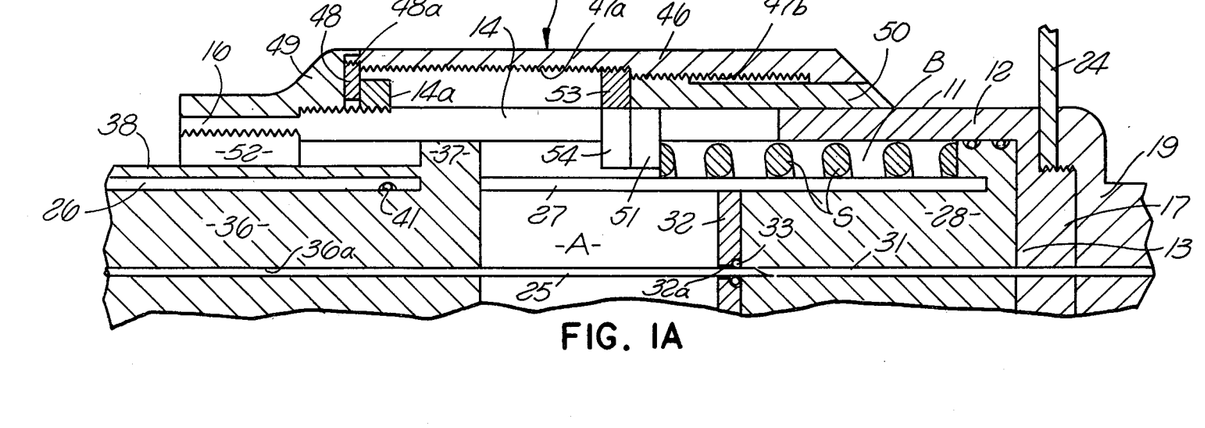
FIG. 1a is an enlarged partial cross-sectional view of the jet injector apparatus of FIG. 1 showing, particularly, the cylindrical medicament apportionment mechanism surrounding the main cylindrical body element of the apparatus.
Figure 2:
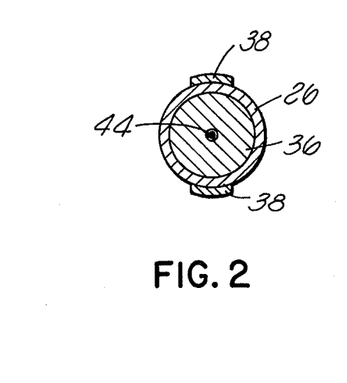
FIG. 2 is a sectional view of the injector apparatus of FIG. 1 taken on line 2—2 of FIG. 1.

A pump cylinder positioning ring 53 is threaded to wall portion 47a of cylinder 46 and is positioned between such cylinder and arcuate legs 14 of tubular member 12 for slideable movement along such legs. The positioning ring 53 is provided with pump stop pawls 54 which project in radial inwardly fashion within slots 15 of tubular member 12. With rotation of the medicament regulating cylinder 46 in one rotary direction the indicia cylinder 50, including pawls 51, will be driven by its threads in a forward direction while the pump cylinder positioning ring 53, including pawls 54, will be driven by its threads in a rearward direction. Reverse rotation of the regulating cylinder 46 will cause the indicia cylinder 50 to be driven in a rearward direction and the pump positioning ring 53 to be driven in a forward direction. The structure and relationship of parts comprising the medicament apportionment mechanism 45, and its relationship with the main cylindrical body mechanism, may be more fully understood by reference to FIG. 1a which is an enlarged view of a portion of FIG. 1.

A power spring S is located in the space B defined by tubular member 12 and piston legs 27 and by the piston head portion 29 of member 28 and pawls 51 of the indicia cylinder 50. This spring may be: designed as a single power unit for applying force between the pawls 51 and the piston head portion 29; or comprised of two or more springs concentrically placed in space B to provide sequential force characteristics to head portion 29; or comprised of two or more springs of differing compression characteristics positioned end to end to provide other desired sequential force patterns to head portion 29.

The rear-most section of tubular member 26 of the internal piston assembly 25 is affixed to and supports a medicament bottle or vial holder 55 through its attachment to bottle holder projection portion 56. The medicament vial holder 55 and projection portion 56 contain a centrally-positioned passageway or orifice 56a which is in alignment with the orifice 36a of pump cylinder 36. At its forward end, orifice 56a leads into a one-way ball valve 57 of well-known ball and spring design. The ball valve 57, as shown in FIG. 1, is positioned in opposing orientation with respect to ball valve 42 of pump cylinder 36. The ball and spring of valve 57 are maintained in seated position at the forward end of vial holder portion 56 by valve cover plate 58 which is affixed to the end of projection portion 56 and has a centrally-positioned, spring opening in alignment with orifice 56a and the intervening ball of valve 57. The ball of valve 57 seats into the end of orifice 56a and is maintained in closed position by its associated spring whereby liquid may be aspirated forwardly through the orifice and through the valve 57, but is precluded from rearward flow through the valve and orifice 56a.

Located within orifice 56a of the vial holder 55 is a cannula 59 which extends from the forward end of the vial holder portion 56, projects through the vial holder 55, projects rearwardly therefrom for a distance sufficient to extend through the stopper of a medicament vial, and terminates in a sharpened point. Adjacent the cannula 59, and projecting from the bottle holder 55, is an air vent cannula 60 of slightly greater projected length than cannula 59. The air vent cannula 60 is likewise sharpened for stopper-piercing action and at its end within bottle holder 55 is in communication with air vent channel 61. Positioned in the bottle holder 55 is a medicament bottle or vial 62 of common configuration including its stopper type closure 63 which has a centrally-located, pierceable diaphragm section 64 through which cannula 59 and air vent cannula 60 extend for communication with the medicament liquid within the bottle or vial seated in the bottle holder 55. A transparent vial holder 62a surrounds vial 62 and is held to the bottle holder 55 by lugs 55a, of common design. The vial holder is of a type whereby vials of varying length, diameter, neck and head size may be inserted into the holder 55 and maintained in appropriate position for liquid aspiration via cannula 59 and air venting via cannula 60.

Considering the operation of the multidose jet injector apparatus as shown in FIGS. 1, 5, 6 and 7, it will be understood that the parts are initially in the position shown in FIG. 1 and described above. In such position the power spring S is fully extended with the piston head portion 29 of the piston assembly 25 directly abutting the internal face of end wall 13 and the piston puller device 35, including medicament pump cylinder 36 and puller legs 38, is in rearward position ready to pull the piston assembly 25 to a cocked position as determined by the position of spring positioning pawls 51 in slots 15 between arcuate cylinder legs 14. The position of pawls 51 has been set by rotation of regulating cylinder 46 of the medicament apportionment mechanism 45 and the rearward retraction of indicia cylinder 50 to its fullest retractable position with pawls 51 abuting pawls 54 of pump positioning ring 53.

Figure 5:
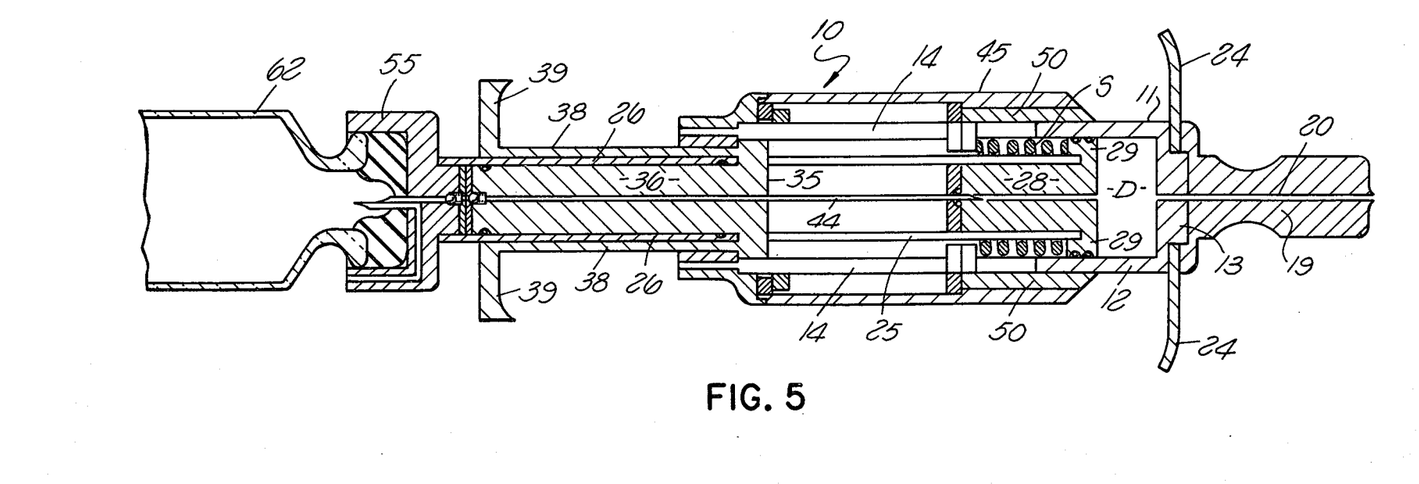
FIG. 5 is a side cross-sectional view of the jet injector apparatus of the invention in which the injector piston element has been pulled to its cocked position by the piston puller element and the medicament pump is in its rearward position whereby the rearward medicament transfer chamber has zero volume and the forward medicament delivery chamber has maximum volume with the power spring fully compressed.

FIG. 5 shows the multidose jet injector apparatus 10 in cocked position with the piston assembly 25 retracted rearwardly to the maximum extent by the piston puller device 35, i.e., the piston pull projections 37 abuting split closure ring 52 and power spring S fully compressed with all coils of the spring in abuting contact with adjacent coils. In its cocked position a medicament delivery chamber D is formed within tubular member 12 between piston head portion 29 and end wall 13. The volume of this chamber, from an injection dosage standpoint, is 1 cc or less. A latching mechanism, not shown but described hereinafter, maintains the piston assembly 25 in its "cocked" position until released at the time of medicament injection.

Figure 6:
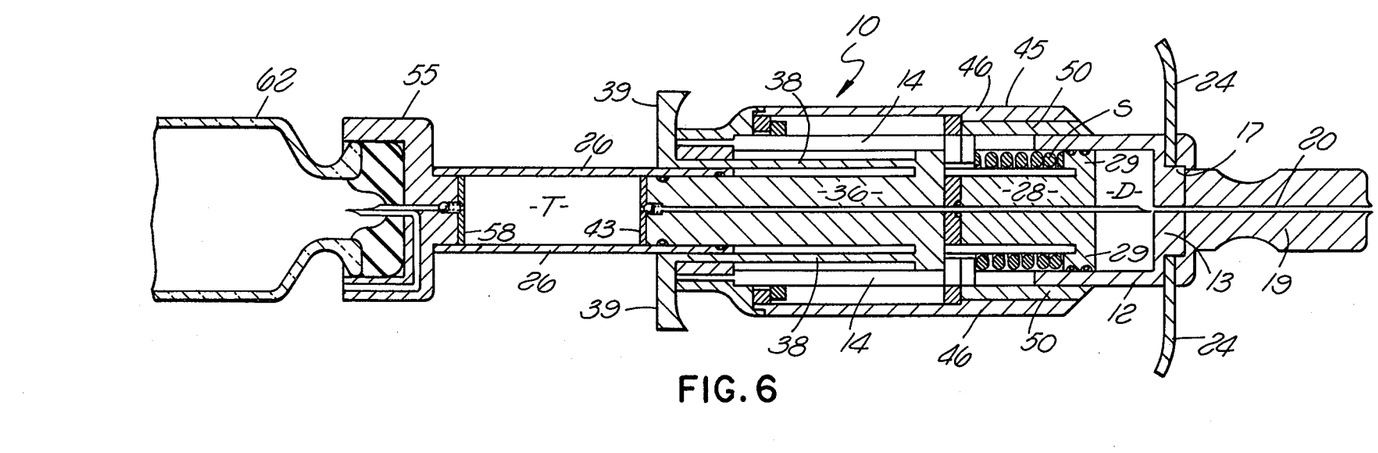
FIG. 6 is a further side cross-sectional view of the jet injector apparatus of the invention in which the injector piston element remains in its cocked position and the medicament pump is in its forward position with medicament liquid drawn into the rearward medicament transfer chamber while the forward medicament delivery chamber remains empty.

FIG. 6 shows the multidose jet injector assembly apparatus in cocked position with the piston puller device 35, and its medicament pump cylinder 36, in a forward position. Movement of the pump cylinder 36 from its FIG. 5 position forwardly to its FIG. 6 position causes aspiration of liquid medicament from vial 62 via cannula 59 and through one-way ball valve 57 to medicament transfer chamber T. Returning the piston puller device 35 (and its medicament pump cylinder 36) to its rearward position, as shown in FIG. 5, causes the liquid medicament volume contained in medicament transfer chamber T to be expressed (pumped) through one-way ball valve 42 and cannula 44 to the medicament delivery chamber D.

With the medicament delivery chamber D filled with medicament liquid, the multidose jet injector apparatus is ready for delivering the medicament by jet injection (needleless) means. Upon release of the latching mechanism, the spring S expands to impart a heavy initial advancing force to the piston assembly 25 and such piston assembly (through its piston head member 28) continues to apply the advancing force for ejecting the medicament liquid through orifice 20 of the nose piece 19 of the jet injector. Following the completion of the medicament injection, the internal piston assembly 25 and the piston puller device 35 are in the positions shown in FIG. 1.

Figure 7:
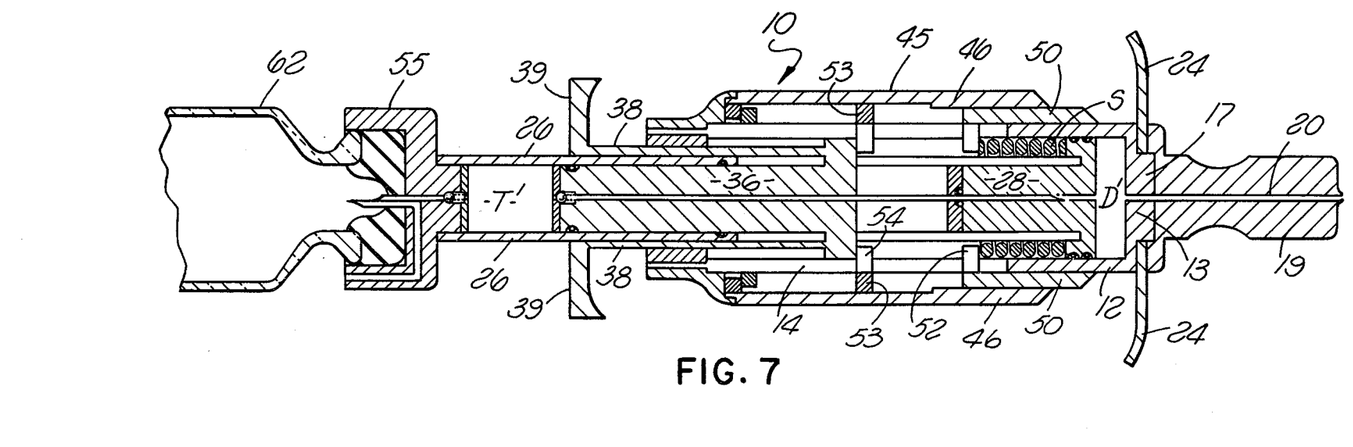
FIG. 7 is another side cross-sectional view of the jet injector apparatus of the invention in which the cylindrical medicament apportionment mechanism has been adjusted for reduced volume dosage with the rearward medicament transfer chamber being of reduced volume and the forward medicament delivery chamber also being of reduced volume.

FIG. 7 shows the multidose injector apparatus 10 of the invention in "cocked" position with the piston assembly 25 retracted rearwardly, but to a lesser extent, as dictated by the forwardly position of pawls 51 of indicia cylinder 50. The indicia cylinder 50 has been moved to its new forwardly position by rotation of the regulating cylinder 46 of the medicament apportionment mechanism 45. With this new setting of the indicia cylinder (and full compression of power spring S) the volume of the delivery chamber D' has been reduced to the extent indicated by the indicia cylinder. In this regard the forward surface of tubular member 11 of the jet injector apparatus will have been inscribed or etched with a series of volume rings and volume indicating designations between the leading edge of indicia cylinder 50 and a point on such tubular member's surface near the hilt grip members 24. Through the rotation of the regulating cylinder 46 (to set the desired reduced volume for delivery chamber D' of FIG. 7) the pump positioning ring 53 (threaded to internal threaded portion 47a of cylinder 46), including pump stop pawls 54, has been moved rearwardly to the position indicated in such figure. The pump stop pawls 54 thereby limit the forward pump position to that shown in FIG. 7 and thereby the volume of transfer chamber T' to the extent that the amount of liquid medicament filling chamber T' after the medicament aspiration step (position of the medicament pump cylinder 36 as shown in FIG. 7) comprises the amount required by the delivery chamber D' at its new volume setting. With the internal piston assembly 25 and the piston puller device 35 and pump cylinder 36 in the positions illustrated in FIG. 7, the jet injector apparatus is ready for manipulation of the piston puller device in a rearward pumping direction to transfer the reduced volume of liquid medicament in transfer chamber T' to the delivery chamber D' as described heretofore.

The multidose jet injector apparatus 10 of the invention has an additional feature in its range of versatility of use. Thus, the apparatus may be manipulated so that two or more different liquid medicaments may be introduced to the forward medicament delivery chamber, mixed therein and injected as a single mixed dose. To accomplish the injection of a mixed medicament dose (two medicaments) through use of the apparatus, the medicament apportionment mechanism 45 is first set (adjustment of the volume of the transfer chamber and the medicament delivery chamber) for receiving the first medicament from its vial or bottle appropriately positioned in the bottle holder 55, for example the setting illustrated in FIG. 7. The apparatus is next "cocked" and the piston puller device 35 is manipulated to aspirate the first medicament into transfer chamber T' and thence transfer it to delivery chamber D'. Following transfer of the first medicament to chamber D', the medicament apportionment mechanism 45 is reset to a greater volume setting which comprises the total volume of the first and second medicaments. This new setting readjusts the respective volumes of the transfer chamber and the delivery chamber and thereafter the first medicament vial is removed from the holder 55 and the second medicament vial seated therein and the apparatus is further "cocked" to the new chamber settings. With the apparatus "cocked" to the new setting the piston puller device is again manipulated to aspirate the second medicament into the transfer chamber and thence to pump same into the delivery chamber for mixing with the first liquid medicament therein and ejection as a mixed dose by release of the piston latch mechanism.

The medicament apportionment mechanism (or volume regulating means 45) mounted on the cylindrical injector body assembly 11 of the jet injector apparatus 10 includes a locking mechanism (not shown in the drawing figures) for maintaining the volume regulating cylinder 46 in a fixed position (after its rotary adjustment to establish the position of the indicia cylinder 50 and volume setting) during the "cocking," medicament transferring and medicament ejecting operations of the injector apparatus. Thus, for example, the cylinder 46 may bear a locking member which (after appropriate rotary adjustment of such cylinder and positioning of indicia cylinder 50) is depressed into one of the slots 15 in tubular member 12 for impeding any further rotational movement of cylinder 46 with respect to the cylindrical injector body assembly and thereby fixes the volume of the medicament delivery chamber (as indicated by the volume reading on tubular member 12 at the leading edge of the indicia cylinder 50).

As previously mentioned, a latching mechanism (not shown in the drawing figures) maintains the piston assembly 25 in its "cocked" position until released at the time of medicament injection. Numerous piston latching mechanisms have been suggested in the prior patent art respecting jet and other injection apparatus. One such latching mechanism has been disclosed in U.S. Pat. No. 2,737,946 issued to G. N. Hein, Jr.

Substantially all of the components and structural elements of the hypodermic jet injector apparatus of the present invention are formed of stainless steel. The O ring seals are of rubber or neoprene composition and the one-way ball valve components (balls and seats) are made of nylon or "Teflon" (DuPont trademark for Polytetrafluorethylene). In most instances the parts and components are mounted together by threaded connection and may be readily disassembled for ease of cleaning. The entire jet injector apparatus is sterilizable.

For proper painless delivery of medicaments, vaccines, anesthetics, and the like, by needleless jet injection techniques, it has been recognized that the injector orifice diameter should range between about 0.002 inches and about 0.02 inches. Further, for most needleless injection of medicaments the force pattern on such medicaments should include two principal force phases, i.e., an initial relatively high pressure force phase of short duration followed by a lower pressure force phase of longer duration. Forces of up to as much as 1,600 to 2,500 psi may be utilized in ejecting the medicament during the initial force phase followed by forces of from 450 to 1,400 psi during the secondary force phase. To develop such force patterns in the jet injection apparatus of the present invention, the injection piston assembly experiences thrust forces of as much as 120 to 150 pounds and the "cocking" action may require a pull force of as much as 30 to 40 pounds.

Other modifications in the structure of the jet injector apparatus will occur to those skilled in the art without departing from the principles of our invention. It is intended that such modifications be embraced by the appended claims as part of the invention.

What is claimed is:

1. A multiple dose hypodermic jet injector for accomplishing the needleless injection of liquid medicaments comprising:
    (a) a cylindrical injector body assembly defining in its forward portion a medicament delivery chamber and terminating at its forward end in a nose piece containing a medicament ejection orifice;
    (b) an injection piston assembly slidably mounted within said body assembly and having a forward piston head portion and an elongated rearward tubular portion defining in its rearward section a medicament transfer chamber, said piston head portion having a central passageway therethrough;
    (c) a medicament reservoir mounted at the rearward end of the tubular portion of said piston assembly and in medicament fluid communication with the transfer chamber of said piston assembly through a first one-way valve;
    (d) spring means for advancing the piston assembly to eject medicament from said delivery chamber and through the medicament ejection orifice;
    (e) a reciprocative medicament pump cylinder enclosed within the elongated rearward tubular portion of said piston assembly, said pump cylinder having a central passageway therethrough and a cannula mounted therein and extending forwardly therefrom within said piston assembly to and into the central passageway of the piston head portion of said assembly for slidable positioning therein and fluid communication therewith, the central passageway of said pump cylinder being in medicament fluid communication with the medicament transfer chamber of said piston assembly through a second one-way valve;
    (f) fluid volume indicia means mounted on said cylindrical body assembly and adjustably positionable thereon, said indicia means including spring seating means which regulate the position of the piston head portion of the injection piston assembly when said assembly is in cocked position with the spring means fully compressed and thereby establishes the volume of the medicament delivery chamber;
    (g) pump cylinder limiting means mounted on said cylindrical body assembly and adjustably positionable thereon, said pump limiting means including pump stop means which regulate the extent of reciprocative movement of said pump cylinder and thereby establishes the volume of the medicament transfer chamber;
    (h) medicament volume regulating means mounted on said cylindrical body assembly in cooperative engagement with said indicia means and said pump limiting means to simultaneously adjust the positions of said indicia means and pump limiting means and thereby adjust and establish the variable like volumes for the medicament delivery chamber and the medicament transfer chamber;

(i) piston puller means connected to the forward end of the reciprocative medicament pump cylinder and extending without the cylindrical injector body assembly for pulling said pump cylinder and the injection piston assembly rearwardly together against the pressure of the spring means to the cocked position established by the fluid volume indicia means and for thereafter reciprocating said pump cylinder first forwardly within the rearward section of said piston assembly to the pump stop means to aspirate liquid medicament from the medicament reservoir through the first one-way valve and into the medicament transfer chamber and thereafter rearwardly within said section of said assembly to pump the medicament from said transfer chamber through the second one-way valve, pump cylinder passageway and cannula, piston head passageway and into the medicament delivery chamber; and (j) a piston latch mechanism for maintaining the injection piston assembly in cocked position against the pressure of the spring means after said assembly has been pulled to such position by the puller means and during the reciprocating movements of said puller to transfer medicament from its reservoir to the delivery chamber and thereafter for releasing said piston assembly whereby said spring means expands to impart force to the piston head portion of said piston assembly with the resulting ejection of the medicament from said delivery chamber and through the medicament ejection orifice of said jet injector.

2. The multiple dose hypodermic jet injector of claim 1 wherein the medicament volume regulating means mounted on the cylindrical injector body assembly includes locking means for maintaining said regulating means in a fixed position after its adjustment to move the indicia means to a desired position and volume setting during the cocking, medicament transferring and medicament injecting operations of said jet injector.

3. The multiple dose hypodermic jet injector of claim 1 wherein the medicament volume regulating means mounted on the cylindrical injector body assembly comprises a rotatable regulating cylinder maintained in fixed longitudinal position with respect to said body assembly during rotation of said cylinder, said cylinder encompassing and being in threaded engagement with the fluid volume indicia means and the pump cylinder limiting means whereby upon rotational movement of said regulating cylinder said indicia means and said limiting means are moved toward or away from each other to establish the desired vatiable like volumes for the medicament delivery chamber and the medicament transfer chamber.

4. The multiple dose hypodermic jet injector of claim 3 wherein the fluid volume indicia means comprises a cylinder surrounding said injector body assembly which is slidable with respect thereto and the spring seating means of said indicia means comprises a multiplicity of circumferentially spaced pawls which extend inwardly from the cylinder through elongated slots in said injector body assembly and which extend inwardly beyond said slots to act as a ring of spaced spring seats.

5. The multiple dose hypodermic jet injector of claim 4 wherein the forward circumferential surface of the cylindrical injector body assembly bears a series of volume indicating rings and appropriate ring markings spaced and positioned so that when the leading edge of the cylinder comprising the fluid volume indicia means corresponds to a given ring the true volume of the medicament delivery chamber will be indicated by the ring marking of said given ring.

6. The multiple dose hypodermic jet injector of claim 3 wherein the pump cylinder limiting means comprises a ring surrounding said injector body assembly which is slidable with respect thereto and the pump stop means of said limiting means comprises a multiplicity of circumferentially spaced pawls which extend inwardly from the ring through elongated slots in said injector body assembly and which extend inwardly beyond said slots to act as a ring of spaced pump stops.

7. The multiple dose hypodermic jet injector of claim 1 wherein the reciprocative medicament pump cylinder within the elongated rearward tubular portion of the injection piston assembly bears at its forward end a multiplicity of circumferentially spaced pull projections which extend outwardly from said pump cylinder through elongated slots in the central section of said piston assembly and which extend outwardly beyond said slots and the piston puller means of the jet injector connect to said pull projections.

8. The multiple dose hypodermic jet injector of claim 7 wherein the piston puller means of the jet injector comprises a pair of pull legs disposed rearwardly along the rear section of the injection piston assembly, at opposite sides of said assembly, from the point of their connection to the pull projections of the medicament pump cylinder to a point rearwardly without the cylindrical injector body assembly, said pull legs terminating at their rearward end in the form of finger grips.

9. The multiple dose hypodermic jet injector of claim 1 wherein the spring means comprises a single coil spring designed so that as it expands after release of the injection piston assembly from its cocked position said spring applies initially a relatively high piston driving force to the piston head portion of said piston assembly for a relatively short period of time and thereafter applies a lower piston driving force to the piston head portion of said piston assembly for a longer period of time during the period in which medicament is ejected from the medicament delivery chamber by said piston assembly.

10. The multiple dose hypodermic jet injector of claim 1 wherein the spring means comprises a pair of coil springs of unequal force value arranged in concentric alignment within said injector and designed so that upon release of the injection piston assembly from its cocked position said springs initially apply a combined relatively high piston driving force to the piston head portion of said piston assembly for a relatively short period of time and thereafter apply a combined lower piston driving force to the piston head portion of said piston assembly for a longer period of time during the period in which medicament is ejected from the medicament delivery chamber by said piston assembly.

11. The multiple dose hypodermic jet injector of claim 1 wherein the spring means comprises a pair of coil springs of unequal force value arranged in end to end alignment within said injector and designed so that upon release of the injection piston assembly from its cocked position said springs initially apply a combined relatively high piston driving force to the piston head portion of said piston assembly for a relatively short period of time and thereafter apply a combined lower piston driving force to the piston head portion of said piston head assembly for a longer period of time during the period in which medicament is ejected from the medicament delivery chamber by said piston assembly.

12. The multiple dose hypodermic jet injector of claim 1 wherein the nose piece of the cylindrical injector body assembly is removable from said body assembly for cleaning and sterilization.

13. The multiple dose hypodermic jet injector of claim 1 wherein the medicament reservoir mounted at the rearward end of the tubular portion of the injection piston assembly comprises a standard multidose medicament vial having a resilient perforatable stopper, said vial being seatable in a vial holder mounted at the rearward end of said tubular portion of said assembly, said holder including a centrally disposed cannula which is sharpened at its extending end for penetration of said vial stopper and which is in communication at its other end with the first one-way valve of said piston assembly.

14. The multiple dose hypodermic jet injector of claim 13 wherein the vial holder includes a centrally disposed air vent cannula which is sharpened at its extending end for penetration of the vial stopper and which is in communication with the atmosphere at its other end whereby air may enter said vial to replace the volume of medicament aspirated from said vial by the forwardly reciprocative movement of the pump cylinder.

* * * * *